United States Patent
Battaglia

(10) Patent No.: US 10,525,004 B2
(45) Date of Patent: Jan. 7, 2020

(54) EPITHELIAL DELIVERY

(75) Inventor: Giuseppe Battaglia, Western Bank (GB)

(73) Assignee: BIOCOMPATIBLES UK LIMITED, Farnham, Surrey (GB)

( * ) Notice: Subject to any disclaimer, the term of this patent is extended or adjusted under 35 U.S.C. 154(b) by 2175 days.

(21) Appl. No.: 12/991,349

(22) PCT Filed: May 14, 2009

(86) PCT No.: PCT/EP2009/055872
§ 371 (c)(1),
(2), (4) Date: Jan. 28, 2011

(87) PCT Pub. No.: WO2009/138477
PCT Pub. Date: Nov. 19, 2009

(65) Prior Publication Data
US 2011/0150941 A1  Jun. 23, 2011

(30) Foreign Application Priority Data
May 15, 2008 (EP) .................... 08156269

(51) Int. Cl.
*A61K 9/00* (2006.01)
*A61K 9/127* (2006.01)
*A61K 47/32* (2006.01)
*A61K 47/34* (2017.01)
*C08F 293/00* (2006.01)

(52) U.S. Cl.
CPC .......... *A61K 9/0014* (2013.01); *A61K 9/1273* (2013.01); *A61K 47/32* (2013.01); *A61K 47/34* (2013.01); *C08F 293/005* (2013.01); *C08F 2438/01* (2013.01)

(58) Field of Classification Search
CPC .... A61K 9/1273; A61K 9/0014; A61K 47/34; A61K 47/32; C08F 293/005
See application file for complete search history.

(56) References Cited

U.S. PATENT DOCUMENTS

| 5,190,762 A * | 3/1993 | Yarosh | 424/450 |
| 2005/0003016 A1 * | 1/2005 | Discher et al. | 424/490 |
| 2008/0305174 A1 * | 12/2008 | Gyurik et al. | 424/497 |
| 2008/0311045 A1 * | 12/2008 | Hardy | 424/9.3 |

OTHER PUBLICATIONS

Vamvakaki Macromolecules Feb. 27, 1999.*
Hannah Lomas et al., "Biomimetic pH Sensitive Polymersomes for Efficient DNA Encapsulation and Delivery", Advanced Materials, 2007, pp. 4238-4243, vol. 19.
Hannah Lomas et al., "Non-cytotoxic polymer vesicles for rapid and efficient intracellular delivery", Faraday Discussions, 2008, pp. 143-159, vol. 139.
Jun Li et al., "Methoxy poly(ethyleneglycol)-block-poly(D,L-lactic acid) copolymer nanoparticles as carriers for transdermal drug delivery", Polymer International, 2008, 268-274, vol. 57.
Jianzhong Du et al., "pH-Sensitive Vesicles Based on a Biocompatible Zwitterionic Diblock Copolymer", Journal of American Chemical Society, 2005, pp. 17982-17983, vol. 127, No. 51.
U.S. Appl. No. 12/991,321, filed Nov. 5, 2010, Andrew Lennard Lewis, et al.
U.S. Appl. No. 12/991,330, filed Nov. 5, 2010, Andrew Lennard Lewis, et al.

* cited by examiner

*Primary Examiner* — David J Blanchard
*Assistant Examiner* — Thurman Wheeler
(74) *Attorney, Agent, or Firm* — Sughrue Mion, PLLC

(57) ABSTRACT

The present invention relates to composition comprising vesicles and associated with the vesicles, a chemical agent, for use in a method of treatment by therapy wherein the chemical agent is delivered trans- and/or intra-epithelially to a human or animal body, wherein the constructs comprise an amphiphilic block copolymer having a hydrophilic and a hydrophobic block.
Methods for forming the composition are also provided.

11 Claims, 5 Drawing Sheets

EPITHELIAL DELIVERY

CROSS REFERENCE TO RELATED APPLICATIONS

This application is a National Stage of International Application No. PCT/EP2009/055872, filed on May 14, 2009, which claims priority from European Patent Application No. 08156269.6, filed on May 15, 2008, the contents of all of which are incorporated herein by reference in their entirety.

FIELD OF THE INVENTION

The invention relates to trans- and intra-epithelial delivery systems for introducing pharmaceutically or cosmetically active ingredients into the human or animal body.

BACKGROUND OF THE INVENTION

Vesicular systems, including liposomes, have been incorporated into many cosmetic formulations. Liposomes are colloidal particles, typically comprising mainly phospholipids and cholesterol. The lipid molecules form bilayers surrounding an aqueous core. Both the bilayer and the core can be used to entrap and present agents to the tissue with which they contact (for instance, the skin). Most studies describe a non-specific targeting effect whereby vesicles allow accumulation of ingredients in the stratum corneum or other upper skin layers. A number of studies have reported enhanced delivery of a variety of pharmaceutical substances, including triamcinolone, methotrexate, hydrocortisone, tretinoin, tacrolimus, rhodamine, cyclosporin and antiandrogens into and through the skin using liposomal formulations.

Transdermal delivery using liposomes as carriers has been illustrated in a few cases where the entrapped drug was able to cross all skin layers (Kato et al., J Pharm. Pharmacol, 1987 39(5): p. 399-400). A number of studies have demonstrated that the vesicle composition, for instance, the inclusion of skin lipids (Fresta et al., J. Drug Target, 1996 4(2): p. 95-101), positively charged lipids (Kitagawa et al., Chem Pharm Bull (Tokyo), 2006 54(2): p. 242-4), and presence of surfactants in the bilayer (Hofland et al., Pharmaceutical Research, 1994 11(5): p. 659-664) may have an effect on substance permeation.

The state of the lipid bilayers of the vesicles, namely the liquid crystal phase or gel phase, also affects dermal and transdermal delivery: liquid crystal state vesicles are thought to be more effective. Such results have been confirmed in vivo (Ogiso et al., Journal of Pharmaceutical Sciences, 1996 85(1): p. 57-64). Other physico-chemical properties, such as particle charge, particle size and lamellarity may also influence the degree of substance transport.

Vesicles other than liposomes have been devised with the aim of improving transdermal and topical delivery of substances. Examples of these include vesicles made of non-ionic surfactants (Niosomes™) (Schreier et al., Journal of Controlled Release, 1994 30(1): p. 1-15), vesicles containing a high percentage of ethanol (ethosomes) (Touitou et al., Drug Development Research, 2000b 50(3-4): p. 406-415) and ultraflexible vesicles otherwise known as transfersomes. Polymersomes (vesicles formed from amphiphilic block copolymers) are the polymeric equivalent of liposomes and because of their macromolecular nature, are known to be much more robust and stable than their lipid counterparts (Discher et al., Science 284 (1991), 1143-6). In addition, their macromolecular nature also allows a very effective tuning of the membrane thickness. Recently, pH sensitive polymersomes have been developed which are able to encapsulate and deliver plasmid DNA to the cell cytosol (Lomas et al., 2007 Adv. Mater 19, 4238-4234).

Liaw et al in Journal of Controlled Release 68 (2000) 273-282, describe percutaneous fentanyl delivery using poly (ethylene oxide)-poly(propylene oxide)-poly(ethylene oxide) gels. The polymer forms micelles which are able to penetrate nude mouse skin within 24 hours.

SUMMARY OF THE INVENTION

In view of the prior art there remains a desire to provide improved trans- and intra-epithelial delivery systems for introducing chemical agents, particularly pharmaceutically or cosmetically active ingredients, into the human or animal body. In accordance with this desire there is provided in a first aspect of this invention a composition comprising vesicles and associated with the vesicles, a chemical agent, for use in a method of treatment by therapy wherein the chemical agent is delivered trans- and/or intra-epithelially to a human or animal body, wherein the vesicles comprise an amphiphilic block copolymer having a hydrophilic and a hydrophobic block.

The second aspect of this invention provides a method for forming a composition according to the first aspect of the invention, wherein one of the blocks of the copolymer is pH sensitive, comprising the steps:

(i) dispersing the amphiphilic copolymer in an aqueous media;
(ii) acidifying the composition formed in step (i);
(iii) adding the chemical agent to the acidified composition; and
(iv) raising the pH to around neutral.

The third aspect of the invention provides an in vitro method of delivering a chemical agent across or into an epithelium comprising contacting a composition as defined in the first aspect of the invention with the epithelium.

The vesicles defined in the first aspect of the invention are biocompatible and do not undergo any cytotoxic interactions with epithelial cells. The vesicle-forming polymer is well accepted by a cell and induces no inflammatory response, and can be used to deliver chemical agents to cells without undue toxicity. Delivery rates are improved compared to the delivery systems described in the prior art.

The invention described herein is concerned with the use of block copolymers that form vesicles for the encapsulation of pharmaceutically and cosmetically active ingredients and for the subsequent delivery of these into and through epithelia.

In this invention membrane-enclosed structures comprising amphiphilic block copolymers are used. These are able to mimic biological phospholipids. Molecular weights of these polymers are much higher than naturally-occurring phospholipid-based surfactants such that they can assemble into more entangled membranes, (Battaglia, G. & Ryan, A. J. J. Am. Chem. Soc. 2005, 127, 8757) providing a final structure with improved mechanical properties and colloidal stability. Furthermore, the flexible nature of the copolymer synthesis allows the application of different compositions and functionalities over a wide range of molecular weights and consequently of membrane thicknesses. Thus the use of these block copolymers as delivery vehicles offers significant advantages over those vehicles used in the prior art.

Rather than using micelles, which have been described in the prior art, the present invention uses vesicles, which are generally formed from a greater number of amphiphilic copolymer units than micelles and have water molecules encapsulated within their core. Vesicles allow a greater number of chemical agents to be encapsulated, and are more effective at dissociating and releasing this chemical agent once taken up into a cell cytosol.

DETAILED DESCRIPTION OF THE INVENTION

Once the vesicles detailed above are taken up into cells, they advantageously dissociate and release the chemical agent within the cell. Dissociation may be promoted by a variety of mechanisms, but is typically promoted by the pH sensitivity of the block copolymer. Preferably, one of the blocks has a pendant group with a $pK_a$ in the range 3.0 to 6.9. Without wishing to be bound by theory, the mechanism of cell internalisation (endocytosis) of the vesicles involves engulfment within phospholipid membranes produced by endocytic organelles such as trafficking vesicles, phagosomes, or pinosomes, depending on the precise endocytic pathway. The endocytic organelle detaches from the cell membrane and takes the vesicles inside the cell for further processing. Regardless of the endocytic pathway, the internalised vesicles experience a reduction in local pH from pH 7.4 to pH 5-6 once inside the organelle. This pH drop is sufficient to trigger the breakdown of active-loaded vesicles and release of chemical agent. As this transition is confined within a semi-permeable organelle membrane, the sudden increase in particle number corresponds to a large increase in osmotic pressure. This causes lysis of the phospolipid membrane of the endocytic organelle, releasing the chemical agent into the cell cytosol.

The composition of this invention is normally aqueous and typically therefore the vesicles are in aqueous solution. A typical pH of the aqueous composition is 7.0 to 7.6, preferably 7.2 to 7.4. Vesicles are generally substantially spherical and comprise a bilayered membrane. The bilayer is generally formed from two layers of amphiphilic molecules, which align to form an enclosed core with hydrophilic head groups facing the core and the exterior of the vesicle, and hydrophilic tail groups forming the interior of the membrane.

A typical diameter of a substantially spherical vesicle is in the range 50-5000 nm. More typically, the diameter is in the range 50-1000 nm. Vesicles having a diameter in this range are normally termed "nanovesicles". The nanovesicles are preferably substantially spherical in shape. Typically, the nanovesicles have a number average diameter of less than 300 nm, preferably less than 250 nm, most preferably less than 200 nm or 150 nm. The thickness of the bilayer is generally between 2 to 50 nm, more typically between 5 and 20 nm. These dimensions can be measured by Transmission Electron Microscopy (T.E.M), and Small Angle X-ray Scattering (SAXS) (Battaglia et al; JACS 127, 8757 (2005)).

The chemical agent is typically associated with the vesicles via physical or chemical interaction, such as electrostatic or hydrophobic attraction. Usually the agent is not covalently bound to the vesicles. The agent may be associated with the interior of the membrane, or with the external surface of membrane-enclosed vesicles. However, preferably the agent is encapsulated within the aqueous core of the vesicles, which are preferably nanovesicles.

A variety of experimental techniques can be used to determine the association between the active agent and the vesicles. For instance, Transmission Electron Microscopy and Dynamic Light Scattering (DLS) can be used to show that the agent is encapsulated within the core of vesicles.

The hydrophobic or the hydrophilic block of the amphiphilic block copolymer preferably comprises pendant groups which have a $pK_a$ in the range 3.0 to 6.9. This confers "pH-sensitivity" on the copolymer. By $pK_a$, is meant the pH where half of the pendant groups are ionised. Typically, the hydrophobic block has the pendant groups with a $pK_a$ in the range 3.0 to 6.9.

Preferably, the $pK_a$ of the pendant groups is in the range 4.0 to 6.9, more preferably 5.5 to 6.9. The vesicles are correspondingly capable of disassociating in such pH ranges.

$pK_a$ can be determined by a variety of methods including pH titration, potentiometric titration, UV spectroscopy and Dynamic Light Scattering (DLS). An appropriate method should be selected to measure the $pK_a$ according to the copolymer which is being analysed and its solubility in the test media.

DLS is the particularly preferred method for measuring $pK_a$. As indicated in the paper by Du et al; J. Am. Chem. Soc 2005, 127, 17982-17983, the DLS signal from $PMPC_{25}$-b-$PDPA_{120}$ copolymer in water varies with pH. At a certain pH the signal rapidly increases as the copolymer undergoes a transition from being molecularly deassociated to associated. The $pK_a$ is taken as the pH of the mid-point of this rapid increase. These experiments are described further in Giacomelli et al, Biomacromolecules 2006, 7, 817-828. In this reference, the experiments are performed on micelles of PMPC-b-PDPA block copolymer, but the techniques may also be used when the phase transition involves vesicle formation.

In the specification, the $pK_a$ of a group in a polymer is determined on the basis of a polymer system (and not assumed to be the same as the $pK_a$'s of similar moieties in non-polymeric systems).

It is preferred that the hydrophobic block comprise pendant cationisable moieties as pendant groups. Cationisable moieties are, for instance, primary, secondary or tertiary amines, capable of being protonated at pH's below a value in the range 3 to 6.9. Alternatively the group may be a phosphine.

In one embodiment of the invention, the hydrophobic block has a degree of polymerisation of at least 50, more preferably at least 70. Preferably, the degree of polymerisation of the hydrophobic block is no more than 250, even more preferably, no more than 200. Typically, the degree of polymerisation of the hydrophilic block is at least 15, more preferably at least 20. It is preferred that the ratio of the degree of polymerisation of the hydrophilic to hydrophobic block is in the range 1:2.5 to 1:8. All of these limitations promote vesicle, rather than micelle formation.

In the invention, although the hydrophilic block may be based on condensation polymers, such as polyesters, polyamides, polyanhydrides, polyurethanes, polyethers (including polyalkylene glycols, especially PEG), polyimines, polypeptides, polyureas, polyacetals or polysaccharides, preferably the hydrophilic block is based on a radical polymerised addition polymer of ethylenically unsaturated monomers. Generally the monomers from which the block is formed themselves have zwitterionic pendant groups which remain unchanged in the polymerisation process. It may alternatively be possible to derivatise a functional pendant group of a monomer to render it zwitterionic after polymerisation.

In one embodiment of the invention, the composition comprises two populations of vesicle, the first of which has a hydrophilic block which is a polyalkylene oxide (preferably PEG) and the second of which has a hydrophilic block which comprises a zwitterionic monomer.

Preferably, the hydrophilic block is formed from ethylenically-unsaturated zwitterionic monomers. Suitable ethylenically unsaturated zwitterionic monomers have the general formula $$YBX \qquad \qquad I$$

In which Y is an ethylenically unsaturated group selected from $H_2C=CR-CO-A-$, $H_2C=CR-C_6H_4-A^1-$, $H_2C=CR-CH_2A^2$, $R^2O-CO-CR=CR-CO-O$, $RCH=CH-CO-O-$, $RCH=C(COOR^2)CH_2-CO-O$,

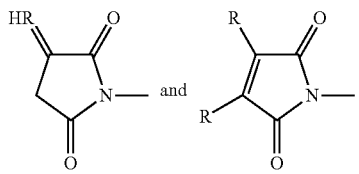

A is —O— or $NR^1$;
$A^1$ is selected from a bond, $(CH_2)_lA^2$ and $(CH_2)_lSO_3^-$ in which l is 1 to 12;
$A^2$ is selected from a bond, —O—, O—CO—, CO—O, CO—$NR^1$—, —$NR^1$—CO, O—CO—$NR^1$—, $NR^1$—CO—O—;
R is hydrogen or $C_{1-4}$ alkyl;
$R^1$ is hydrogen, $C_{1-4}$- alkyl or BX;
$R^2$ is hydrogen or $C_{1-4}$ alkyl;
B is a bond, or a straight branched alkanediyl, alkylene oxaalkylene, or alkylene (oligooxalkylene) group, optionally containing one or more fluorine substituents;
X is a zwitterionic group.

Preferably X is an ammonium, phosphonium, or sulphonium phosphate or phosphonate ester zwitterionic group, more preferably a group of the general formula II

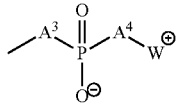

in which the moieties $A^3$ and $A^4$, which are the same or different, are —O—, —S—, —NH— or a valence bond, preferably —O—, and $W^+$ is a group comprising an ammonium, phosphonium or sulphonium cationic group and a group linking the anionic and cationic moieties which is preferably a $C_{1-12}$-alkanediyl group,
preferably in which $W^+$ is a group of formula

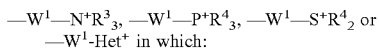

$W^1$ is alkanediyl of 1 or more, preferably 2-6 carbon atoms optionally containing one or more ethylenically unsaturated double or triple bonds, disubstituted-aryl (arylene), alkylene arylene, arylene alkylene, or alkylene aryl alkylene, cycloalkanediyl, alkylene cycloalkyl, cycloalkyl alkylene or alkylene cycloalkyl alkylene, which group $W^1$ optionally contains one or more fluorine substituents and/or one or more functional groups; and
either the groups $R^3$ are the same or different and each is hydrogen or alkyl of 1 to 4 carbon atoms, preferably methyl, or aryl, such as phenyl, or two of the groups $R^3$ together with the nitrogen atom to which they are attached form an aliphatic heterocyclic ring containing from 5 to 7 atoms, or the three groups $R^3$ together with the nitrogen atom to which they are attached as heteroaromatic ring having 5 to 7 atoms, either of which rings may be fused with another saturated or unsaturated ring to form a fused ring structure containing from 5 to 7 atoms in each ring, and optionally one or more of the groups $R^3$ is substituted by a hydrophilic functional group, and the groups $R^4$ are the same or different and each is $R^3$ or a group $OR^3$, where $R^3$ is as defined above; or Het is an aromatic nitrogen-, phosphorus- or sulphur-, preferably nitrogen-, containing ring, for example pyridine.

Monomers in which X is of the general formula in which $W^+$ is $W^1N^+R^3_3$ may be made as described in our earlier specification WO-A-9301221. Phosphonium and sulphonium analogues are described in WO-A-9520407 and WO-A-9416749.

Generally a group of the formula II has the preferred general formula III

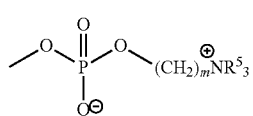

where the groups $R^5$ are the same or different and each is hydrogen or $C_{1-4}$ alkyl, and m is from 1 to 4, in which preferably the groups $R^5$ are the same preferably methyl.

In phosphobetaine based groups, X may have the general formula IV

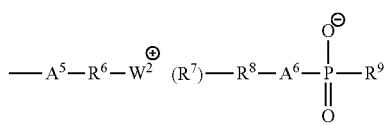

in which $A^5$ is a valence bond, —O—, —S— or —NH—, preferably —O—;

$R^6$ is a valence bond (together with $A^5$) or alkanediyl, —C(O)alkylene- or —C(O)NH alkylene preferably alkanediyl, and preferably containing from 1 to 6 carbon atoms in the alkanediyl chain;

$W^2$ is S, $PR^7$ or $NR^7$;

the or each group $R^7$ is hydrogen or alkyl of 1 to 4 carbon atoms or the two groups $R^7$ together with the heteroatom to which they are attached form a heterocyclic ring of 5 to 7 atoms;

$R^8$ is alkanediyl of 1 to 20, preferably 1 to 10, more preferably 1 to 6 carbon atoms;

$A^6$ is a bond, NH, S or O, preferably O; and $R^9$ is a hydroxyl, $C_{1-12}$ alkyl, $C_{1-12}$ alkoxy, $C_{7-18}$ aralkyl, $C_{7-18}$-aralkoxy, $C_{6-18}$ aryl or $C_{6-18}$ aryloxy group.

Monomers comprising a group of the general formula IV may be made by methods as described in JP-B-03-031718, in which an amino substituted monomer is reacted with a phospholane.

In compounds comprising a group of the general formula IV, it is preferred that $A^5$ is a bond;
$R^6$ is a $C_{2-6}$ alkanediyl;
$W^2$ is $NR^7$:
each $R^7$ is $C_{1-4}$ alkyl;
$R^8$ is $C_{2-6}$ alkanediyl;
$A^6$ is O; and
$R^9$ is $C_{1-4}$ alkoxy.

Alternatively X may be a zwitterion in which the anion comprises a sulphate, sulphonate or carboxylate group.

One example of such a group is a sulphobetaine group, of the general formula V $$-\underset{R^{10}}{\overset{R^{10}}{\overset{|}{\overset{\oplus}{N}}}}-(CH_2)_sSO_3^{\ominus} \qquad V$$

where the groups $R^{10}$ are the same or different and each is hydrogen or $C_{1-4}$ alkyl and s is from 2 to 4.

Preferably the groups $R^{10}$ are the same. It is also preferable that at least one of the groups $R^{10}$ is methyl, and more preferable that the groups $R^{36}$ are both methyl.

Preferably s is 2 or 3, more preferably 3.

Another example of a zwitterionic group having a carboxylate group is an amino acid moiety in which the alpha carbon atom (to which an amine group and the carboxylic acid group are attached) is joined through a linker group to the backbone of the biocompatible polymer. Such groups may be represented by the general formula VI $$-A^7\underset{R^{11}}{\overset{\overset{\oplus}{NR^{12}_3}}{\overset{|}{\underset{H}{C}}}}\overset{}{CO_2^{\ominus}} \qquad VI$$

in which $A^7$ is a valence bond, —O—, —S— or —NH—, preferably —O—, $R^{11}$ is a valence bond (optionally together with $A^7$) or alkanediyl, —C(O)alkylene- or —C(O)NHalkylene, preferably alkanediyl and preferably containing from 1 to 6 carbon atoms; and the groups $R^{12}$ are the same or different and each is hydrogen or alkyl of 1 to 4 carbon atoms, preferably methyl, or two or three of the groups $R^{12}$, together with the nitrogen to which they are attached, form a heterocyclic ring of from 5 to 7 atoms, or the three group $R^{12}$ together with the nitrogen atom to which they are attached form a fused ring heterocyclic structure containing from 5 to 7 atoms in each ring.

Another example of a zwitterion having a carboxylate group is a carboxy betaine —$N^+(R^{13})_2(CH_2)_rCOO^-$ in which the $R^{13}$ groups are the same or different and each is hydrogen or $R_{1-4}$ alkyl and r is 2 to 6, preferably 2 or 3.

In the zwitterionic monomer of the general formula I it is preferred that the ethylenic unsaturated group Y is $H_2C=CR$—CO-A-. Such acrylic moieties are preferably methacrylic, that is in which R is methyl, or acrylic, in which R is hydrogen. Whilst the compounds may be (meth)acrylamido compounds (in which A is $NR^1$), in which case $R^1$ is preferably hydrogen, or less preferably, methyl, most preferably the compounds are esters, that is in which A is O.

In monomers of the general formula I, especially where Y is the preferred (alk)acrylic group, B is most preferably an alkanediyl group. Whilst some of the hydrogen atoms of such group may be substituted by fluorine atoms, preferably B is an unsubstituted alkanediyl group, most preferably a straight chain group having 2 to 6 carbon atoms.

A particularly preferred zwitterionic monomer is 2-methacryloyloxyethyl-phosphorylcholine (MPC). Mixtures of zwitterionic monomers each having the above general formula may be used.

The hydrophobic block may be formed of condensation polymers, such as polyethers (including polyalkylene glycols), polyesters, polyamides, polyanhydrides, polyurethanes, polyimines, polypeptides, polyureas, polyacetals, or polysiloxanes. One example of a suitable hydrophobic block is polyalkylene oxide, usually polypropylene oxide, that is the same type of block as has been used in the well-studied Pluronic/Poloxamer based systems. One type of highly hydrophobic block is poly(dimethylsiloxane). In one preferred embodiment the type of polymer forming the hydrophobic block is the same as that forming the hydrophilic block. Preferably the polymer is formed by radical polymerisation of ethylenically unsaturated monomers.

Suitable monomers from which the hydrophobic block may be formed have the general formula VII $$Y^1B^1Q \qquad VII$$

in which $Y^1$ is selected from $H_2C=CR^{14}$—CO-$A^8$-, $H_2C=CR^{14}$—$C_6H_4$-$A^9$-, $H_2C=CR^{14}$—$CH_2A^{10}$, $R^{16}O$—CO—$CR^{14}=CR^{14}$—CO—O, $R^{14}CH=CH$—CO—O—, $R^{14}CH=C(COOR^{16})CH_2$—CO—O,

[structures of two pyrrolidine-dione derivatives shown with $HR^{40}$ and $R^{40}$ substituents] and $A^8$ is —O— or $NR^{15}$;
$A^9$ is selected from a bond, $(CH_2)_qA^{10}$ and $(CH_2)_qSO_3^-$ in which q is 1 to 12;
$A^{10}$ is selected from a bond, —O—, O—CO—, CO—O—, CO—$NR^{15}$—,
—$NR^{15}$—CO—, O—CO—$NR^{15}$—, $NR^{15}$—CO—O—;
$R^{14}$ is hydrogen or $C_{1-4}$ alkyl;
$R^{15}$ is hydrogen, $C_{1-4}$ alkyl or $B^1Q$;
$R^{16}$ is hydrogen or $C_{1-4}$ alkyl;
$B^1$ is a bond, or a straight branched alkanediyl, alkylene oxaalkylene, or alkylene (oligooxalkylene) group, optionally containing one or more fluorine substituents; and Q is a cationic or cationisable group of the formula —$NR^{17}_p$, —$PR^{17}_p$ and $SR^{17}_r$, in which p is 2 or 3, r is 1 or 2, the groups $R^{43}$ are the same or different and each is selected from the group consisting of hydrogen, $C_{1-24}$ alkyl and aryl, or two of the groups $R^{17}$ together with the heteroatom to which they are attached from a 5 to 7 membered heterocyclic ring or three $R^{17}$ groups together with the heteroatom to which they are attached form a 5 to 7 membered heteroaromatic ring, either of which rings may be fused to another 5 to 7 membered saturated or unsaturated ring, and any of the $R^{43}$ groups may be substituted by amino or hydroxyl groups or halogen atoms; wherein if p is 3, at least one of the groups $R^{17}$ must be hydrogen.

Preferably $Y^1$ is $H_2C\!=\!CR^{14}\!-\!CO\!-\!A^8\!-$ where $R^{14}$ is H or methyl and $A^8$ is O or NH.

Preferred groups $B^1$ are alkanediyl, usually with linear alkyl chains and preferably having 2 to 12 carbon atoms, such as 2 or 3 carbon atoms.

Preferably Q is $NR^{17}_2$ where $R^{17}$ is $C_{1\text{-}12}$-alkyl. Preferably both $R^{17}$'s are the same. Particularly useful results have been achieved where the groups $R^{17}$ are $C_{1\text{-}4}$ alkyl, especially ethyl, methyl or isopropyl.

Either or both the hydrophobic and hydrophilic blocks may include comonomers, for instance to provide functionality, control over hydrophobicity, control over pH sensitivity, $pK_a$ or $pK_b$ as the case may be, control over temperature sensitivity or as general diluents. For instance comonomers providing functionality may be useful to provide conjugation of pendant groups following polymerisation and/or vesicles formation, to targeting moieties, or to provide for conjugation between the biologically active molecule and the polymer. Alternatively, functional groups may allow for crosslinking of the polymer following vesicle formation, to confer increased stability on the vescles structure.

Examples of suitable comonomers are compounds of the general formula VIII

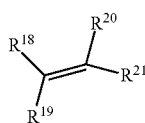

VIII in which $R^{18}$ is selected from hydrogen, halogen, $C_{1\text{-}4}$ alkyl and groups $COOR^{22}$ in which $R^{22}$ is hydrogen and $C_{1\text{-}4}$ alkyl;

$R^{19}$ is selected from hydrogen, halogen and $C_{1\text{-}4}$ alkyl;

$R^{20}$ is selected from hydrogen, halogen, $C_{1\text{-}4}$ alkyl and groups $COOR^{22}$ provided that $R^{18}$ and $R^{20}$ are not both $COOR^{22}$; and $R^{21}$ is a $C_{1\text{-}10}$ alkyl, a $C_{1\text{-}20}$ alkoxycarbonyl, a mono-or di-($C_{1\text{-}20}$ alkyl) amino carbonyl, a $C_{6\text{-}20}$ aryl (including alkaryl) a $C_{7\text{-}20}$ aralkyl, a $C_{6\text{-}20}$ aryloxycarbonyl, a $C_{1\text{-}20}$ -aralkyloxycarbonyl, a $C_{6\text{-}20}$ arylamino carbonyl, a $C_{7\text{-}20}$ aralkyl-amino, a hydroxyl or a $C_{2\text{-}10}$ acyloxy group, any of which may have one or more substituents selected from halogen atoms, alkoxy, oligo-alkoxy, aryloxy, acyloxy, acylamino, amine (including mono and di-alkyl amino and trialkylammonium in which the alkyl groups may be substituted), carboxyl, sulphonyl, phosphoryl, phosphino, (including mono- and di-alkyl phosphine and tri-alkylphosphonium), zwitterionic, hydroxyl groups, vinyloxycarbonyl and other vinylic or allylic substituents, and reactive silyl or silyloxy groups, such as trialkoxysilyl groups;

or $R^{21}$ and $R^{20}$ or $R^{21}$ and $R^{19}$ may together form $-CONR^{23}CO$ in which $R^{23}$ is a $C_{1\text{-}20}$ alkyl group.

It is preferred for at least two of the groups $R^{18}$, $R^{19}$, $R^{20}$ and $R^{21}$ to be halogen or, more preferably, hydrogen atoms. Preferably $R^{18}$ and $R^{19}$ are both hydrogen atoms. It is particularly preferred that compound of general formula X be a styrene-based or acrylic based compound. In styrene based compounds $R^{21}$ represents an aryl group, especially a substituted aryl group in which the substituent is an amino alkyl group, a carboxylate or a sulphonate group. Where the comonomer is an acrylic type compound, $R^{21}$ is an alkoxy-carbonyl, an alkyl amino carbonyl, or an aryloxy carbonyl group. Most preferably in such compounds $R^{21}$ is a $C_{1\text{-}20}$ -alkoxy carbonyl group, optionally having a hydroxy substituent. Acrylic compounds are generally methacrylic in which case $R^{20}$ is methyl.

Preferably the comonomer is a non-ionic comonomer, such as a $C_{1\text{-}24}$ alkyl(alk)-acrylate or -acrylamide, mono- or di- hydroxy-$C_{1\text{-}6}$-alkyl(alk)-acrylate, or acrylamide, oligo ($C_{2\text{-}3}$ alkoxy) $C_{2\text{-}18}$-alkyl (alk)-acrylate, or -acrylamide, styrene, vinylacetate or N-vinyllactam.

For optimum vesicle formation, the block copolymers should have controlled molecular weights. It is preferable for each of the blocks to have molecular weight controlled within a narrow band, that is, to have a narrow polydispersity. The polydispersity of molecular weight should, for instance, be less than 2.0, more preferably less than 1.5, for instance in the range 1.1 to 1.4.

Of course, in the preferred embodiment of this invention wherein one of the blocks has a $pK_a$ is in the range 3.0 to 6.9, the blocks should be selected so that they have the requisite $pK_a$.

In one embodiment of this invention, the monomer from which the hydrophobic block is formed 2-(diisopropylamino)ethyl methacrylate (DPA) or 2-(diethylamino)ethyl methacrylate (DEA). In another embodiment, the hydrophilic block is PMPC. Preferably, the copolymer is a PMPC-b-PDPA block copolymer. Preferably, the block copolymer has general formula PMPC$_m$-b-PDPA$_n$, wherein m is in the range 15-30 (for instance, 25) and n is 50 to 180 or 70 to 180, preferably 100 to 160, more preferably 120 to 160.

Typically, the hydrophobic block is not formed from 2-(dimethyl)aminoethyl methacrylate (DMA) monomers.

The block copolymer may be a simple A-B block copolymer, or may be an A-B-A or B-A-B block copolymer (where A is the hydrophilic block and B is the hydrophobic block). It may also be an A-B-C, A-C-B or B-A-C block copolymer, where C is a different type of block. C blocks may, for instance, comprise functional, e.g. cross-linking or ionic groups, to allow for reactions of the copolymer, for instance in the novel compositions. Crosslinking reactions especially of A-C-B type copolymers, may confer useful stability on nanovesicles. Cross-linking may be covalent, or sometimes, electrostatic in nature. Cross-linking may involve addition of a separate reagent to link functional groups, such as using a difunctional alkylating agent to link two amino groups. The block copolymer may alternatively be a star type molecule with hydrophilic or hydrophobic core, or may be a comb polymer having a hydrophilic backbone (block) and hydrophobic pendant blocks or vice versa. Such polymers may be formed by instance by the random copolymerisation of monounsaturated macromers and monomers.

The details of the process for polymerising the monomers which are used in this invention are to be found in WO 03/074090.

The living radical polymerisation process has been found to provide polymers of zwitterionic monomers having a polydispersity (of molecular weight) of less than 1.5, as judged by gel permeation chromatography. Polydispersities in the range 1.2 to 1.4 for the or each block are preferred.

An advantage of the present invention where one of the blocks is pH sensitive, is that the vesicles may be loaded using a pH change system. In such a process, polymer is dispersed in aqueous liquid in ionised form, in which it solubilises at relatively high concentrations without forming vesicles. Subsequently the pH is changed such that some or all of the ionised groups become deprotonated so that they are in non-ionic form. At this second pH, the hydrophobicity of block increases and vesicles are formed spontaneously.

The method of forming vesicles with associated chemical agent (generally encapsulated in their core), wherein one of the blocks of the copolymer is pH sensitive, may involve the following steps:

(i) dispersing the amphiphilic copolymer in an aqueous media;

(ii) acidifying the composition formed in step (i);

(iii) adding the chemical agent to the acidified composition; and (iv) raising the pH to around neutral.

This method preferably comprises a preliminary step wherein the amphiphilic copolymer is dissolved in an organic solvent in a reaction vessel and the solvent is then evaporated to form a film on the inside of the reaction vessel.

By "pH sensitive", it is meant that one of the blocks has a group which becomes protonated/deprotonated at a particular pH. Preferably, one of the blocks, and typically the hydrophobic block comprises pendant groups which have a $pK_a$ in the range 3.0 to 6.9, for instance, 4.0 to 6.9. Step (ii) of acidifying the composition, typically reduces the pH to a value below the $pK_a$ of the pendant group.

In more detail, vesicles are typically prepared by dissolving copolymer in an organic solvent, such as a 2:1 chloroform:methanol mix in a glass container. If the chemical agent is water insoluble, it is then typically added at this stage. Solvent can be evaporated under vacuum leaving a copolymeric film deposited on the walls of the container. The film is then re-hydrated with an aqueous solution, for instance using phosphate buffer saline. The pH of the resultant suspension is decreased to a pH of around 2, to solubilise the film, and then increased slowly to around a pH of 6. Once the pH has reached this value, a water soluble chemical agent may be added. The pH is then increased to around neutral, to encapsulate the agent. The dispersion may then be sonicated and extruded, for instance using a bench top extruder. UV spectroscopy may be used to calculate encapsulation efficiency, using techniques well known in the art.

An alternative method for forming vesicles with encapsulated chemical agent may involve simple equilibration of the chemical agent and vesicles in water. For instance chemical agent may be contacted in solid form with an aqueous dispersion of polymer vesicles and incubated, optionally with shaking, to solubilise the active in the dispersed vesicles. Alternatively, chemical agent dissolved in organic solvent may be emulsified into an aqueous dispersion of polymer vesicles, whereby solvent and agent become incorporated into the core of the vesicles, followed by evaporation of solvent from the system.

The vesicles used in the invention may be formed from two or more different block copolymers. For instance, they may be formed from a block copolymer comprising a polyalkylene oxide hydrophilic block, and from a block copolymer which has a hydrophilic block comprising a zwitterionic monomer. In this embodiment, in the method of forming vesicles, a mixture of the two block copolymers is used. A suitable mixture would be, for instance, a 75:25 ratio by weight of PMPC-PDPA and PEO-PDPA.

Generally, 0.01% to 10% (w/w) of chemical agent is mixed with copolymer in the methods described above.

The vesicles are used in this invention to deliver pharmaceutically and cosmetically active ingredients across or into an epithelial layer into the human or animal body.

By epithelium, is meant a membranous cellular tissue that covers a free surface or lines a tube or cavity of a human or animal body and serves especially to enclose and protect the other parts of the body, to produce secretions and to function in assimilation. Such tissue which are isolated from the human or animal body, or grown in culture in vitro, including epithelial models known in the art, are also encompassed within the term "epithelium".

There are many different types of epithelial cells, including squamous, cuboidal, columnar and transitional. An epithelial layer may be simple (comprise a single layer of cells), stratified (comprise more than one layer of cells) or be pseudostratified with cilia (single layer of cells with cilia).

Epithelial cells line most of the digestive system, the female and male reproductive system, the respiratory and urinary system, as well as form the skin. The outermost layer of human skin is composed of dead stratified, keratinized epithelial cells. This is known as the epidermis.

Preferably, the vesicles in this invention are used in the delivery of chemical agents across the epidermis, oral mucosa or buccal cavity. In a further preferred embodiment, the vesicles are used in bronchial delivery, whereby the vesicles enter the body by inhalation.

As detailed above, epithelia may comprise more than one layer of cell. The composition of vesicles can be tailored for delivery across epithelia in order to immediately target cells in the upper layers, or to allow transport and diffusion through the layers to the lower levels. Preferably, at least a proportion of the vesicles enter the epithelial cells and release chemical agent within the cell cytosol. In this specification this is referred to as "intra-epithelial" delivery. For instance, when the chemical agent is an anti-fungal and the vesicles are applied to the skin, it is important than the chemical agent is released both between and within the cells, to ensure that all infection is eradicated. In an alternative embodiment, the vesicles pass completely through the epithelium. This is termed "trans-epithelial" delivery. An example of such an embodiment is the delivery of chemical agents through the intestinal wall to the bloodstream. Intra- and trans-epithelial delivery may occur simultaneously.

Alternatively the vesicles of the invention may be targeted to the gut epithelium itself. Chemical agents may be delivered to the cells of the gut epithelium to treat disease states such as inflammatory bowel disease, for instance.

Vesicles which have a hydrophilic block which comprises a zwitterionic monomer, particularly PMPC are readily taken up by cells in the upper layers of epithelia whereas vesicles which have a PEG hydrophilic block have a slower uptake. Thus, by using a mixture of vesicles having different hydrophilic blocks, the diffusion of the vesicles through the skin can be controlled.

The chemical agent is any entity which can be associated with the vesicles and is desirably delivered across an epithelium. Preferably the chemical agent is encapsulated inside the vesicles. The chemical agent may be, for instance, a pharmaceutically or cosmetically active ingredient. It may alternatively be an imaging agent. In one embodiment of the invention, an imaging agent acts as a "reporter molecule" and is delivered to the epithelium along with one or more different chemical agents.

The chemical agent may be conjugated to an imaging agent such as a fluorescent dye. In a further embodiment, an active and an imaging agent are independently associated with the vesicles.

A suitable imaging agent for use in the present invention is any label which fluoresces when excited with electromagnetic radiation, and can be associated with the vesicles. Typically, the fluorescent label is encapsulated within the aqueous core of vesicles. However, when the fluorescent label is hydrophobic, more typically it is associated with the hydrophobic membrane. Fluorescent dyes, such as rhodamine, fluorescein, BODIPY® and NBD are particularly suitable.

When the active ingredient is cosmetically active, the composition may be referred to as a cosmetic composition and may further comprise one or more dermatologically acceptable adjuvants.

In one embodiment of this invention, the composition is a cosmetic composition, and the cosmetically active ingredient is an antioxidant, such as Coenzyme $Q_{10}$ or Vitamin C. The encapsulation of antioxidants may enhance their solubility, stability and delivery, and improve their distribution within the skin. Since most antioxidants are water insoluble, the delivery of these compounds through existing liposomes and other topical preparations such as creams and gels is poor due to the barrier nature of the skin.

In the cosmetic composition according to this invention, the one or more dermatologically acceptable adjuvants should not produce irritating side-effects on the skin. The composition may be in the form of an aqueous gel, a solid product such as a compacted powder or alternatively be in the form of a stick. The adjuvants may comprise vitamins, hormones, antioxidants, preserving agents, fillers, fragrances, thickeners, moisturisers, wetting agents, anionic, non-ionic or amphoteric polymers and further cosmetic or dermatological active agents. The fillers may be in the form of very fine powders and can be of natural or synthetic origin. Fillers include mineral powders such as talc, plant powders such as corn starch powder or organic powders such as nylon or polyester powder. Beside fillers, dyes and pigments may also form part of the cosmetic composition.

When the active ingredient is pharmaceutically active, the composition of the invention may be referred to as a pharmaceutical composition and may further comprise one or more pharmaceutically acceptable excipients.

The pharmaceutically active ingredient may be, for instance, an antibiotic, an antifungal, an anticancer or immunosuppressive agent, a local anaesthetic, antiviral, antiseptic, antipruritic, parasiticidal compound, corticosteroid or a treatment for eczema, psoriasis, warts, calluses, alopecia and erectile disfunction.

The composition may be in the form of a solution, dispersion, cream, gel, implant, ointment, emulsion, suspension, powder, paste, patch, capsule, suppository, spray or aerosol. Preferably, the composition is in the form of a cream to be applied to the skin. The vesicles may be dispersed in a pharmaceutically acceptable cream, ointment or gel. For instance, the vesicles may be in aqueous suspension. Alternatively, the composition according to the first aspect of the invention may be dried, and the pharmaceutical composition thereby provided in a form of a powder.

Pharmaceutically acceptable excipients suitable for use in such compositions are well known in the art.

In therapeutic use, the composition may be administered orally, intravenously, rectally, parenterally, by inhalation, topically, transdermally, ocularly, nasally or to the buccal cavity. Topical administration is preferred. Preferably, the composition passes through skin.

The vesicles associated with chemical agent (or "active") are contacted with cells in a manner such as to promote uptake of the vesicles by the cells. In vitro, typically, the cells are grown in culture medium and then seeded onto suitable composites such as those based on human sterilised allodermis (Chakrabary et al; Br J Dermatol. 1999, 141 (5): 811-23). The vesicles are then added directly to the cells on the support. Typically, a known volume of aqueous dispersion of vesicles (for instance, 5-20 mg/ml in PBS) is added to the cells in their culture media.

The cells which are contacted with the active-loaded vesicles may be human or animal epithelial cells.

The invention will now be illustrated by the following Examples and Figures, wherein.

Figure 7:
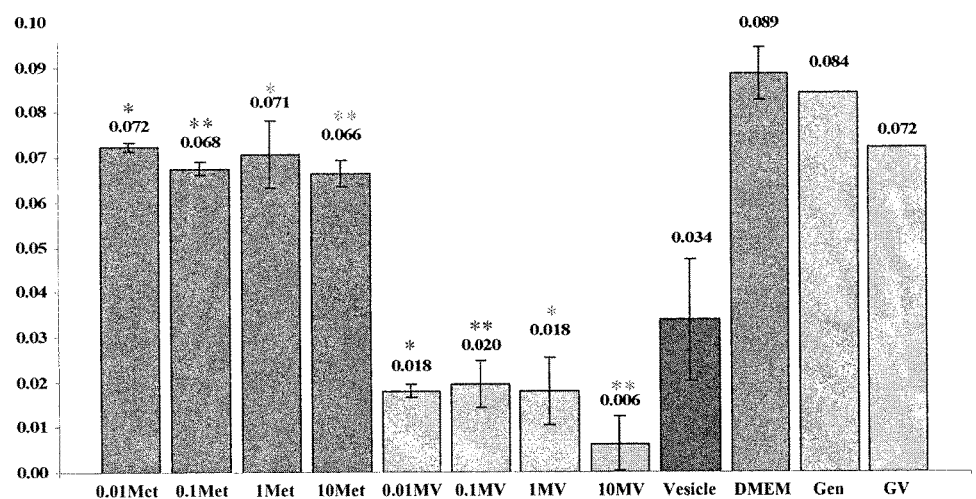
Figure 8:
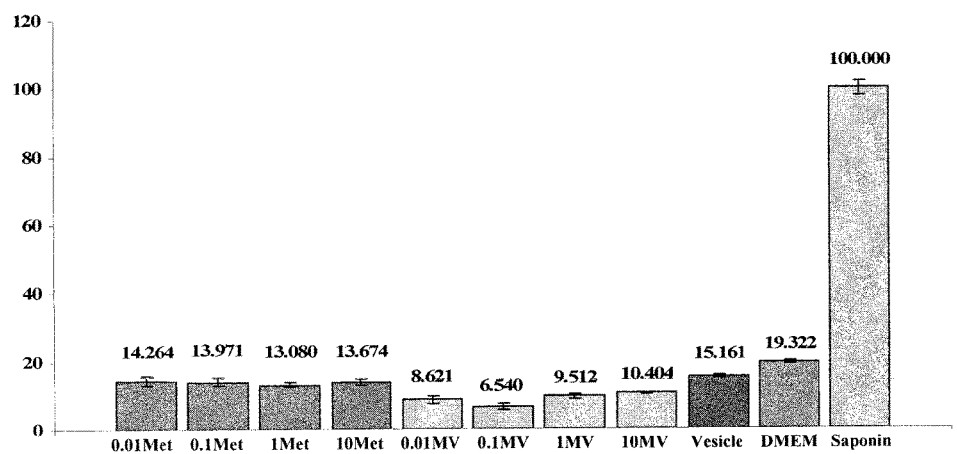

FIG. 7 shows the recovered intracellular *P. gingivalis* after treatment with increasing concentration of free metronidazole (Met), encapsulated metronidazole (MV), vesicles (Vesicle) only or DMEM, gentamycin (Gen) and encapsulated gentamycin (GV) (Y axis=% cell invasion); and FIG. 8 shows the non-viable H-357 cells after treatment with increasing concentration of free metronidazole (Met), encapsulated metronidazole (MV), vesicles only (Vesicle) or DMEM, gentamycin (Gen) and encapsulated gentamycin (GV) (Y axis=% cell death).

EXAMPLES

Example 1

Copolymer Synthesis 2-(Methacryloyloxy)ethyl phosphorylcholine (MPC; >99%) was used as received (Biocompatibles UK Ltd). 2-(Diisopropylamino)ethyl methacrylate (DPA) was purchased from Scientific Polymer Products (USA). Copper (I) bromide (CuBr; 99.999%), 2,2'-bipyridine (bpy), methanol and isopropanol were purchased from Aldrich and were used as received. The silica used for removal of the ATRP copper catalyst was column chromatography grade silica gel 60 (0.063-0.200 mm) purchased from E. Merck (Darmstadt, Germany). 2-(N-Morpholino)ethyl 2-bromo-2-methylpropanoate (ME-Br) initiator was synthesized according to a previously reported procedure (Robinson, K. L., et al, *J. Mater. Chem.* 2002, 12, 890).

$PMPC_{25}$-$PDPA_{70}$ copolymer was synthesized by an ATRP procedure, as reported elsewhere (Du, J., et al, *J. Am. Chem. Soc.* 2005, 127, 17982). Briefly, a Schlenk flask with a magnetic stir bar and a rubber septum was charged with Cu (I) Br (25.6 mg, 0.178 mmol) and MPC (1.32 g, 4.46 mmol). ME-Br initiator (50.0 mg, 0.178 mmol) and bpy ligand (55.8 mg, 0.358 mmol) were dissolved in methanol (2 ml), and this solution was deoxygenated by bubbling $N_2$ for 30 minutes before being injected into the flask using a syringe. The [MPC]:[ME-Br]:[CuBr]:[bpy] relative molar ratios were 25:1:1:2. The reaction was carried out under a nitrogen atmosphere at 20° C. After 65 minutes, deoxygenated DPA (6.09 g, 28.6 mmol) and methanol (7 ml) mixture was injected into the flask. After 48 h, the reaction solution was diluted by addition of isopropanol (about 200 ml) and then passed through a silica column to remove the catalyst.

For the synthesis of PEO-PDPA, the procedure followed Vamvakaki et al in Macromolecules; 1999; 32(6) pp 2088-2090 was adapted, as detailed below.

The monohydroxy-capped poly(ethylene oxide) (PEO) was donated by Inspec U.K. GPC analyses gave Mw/Mn's of 1.10 for PEO; degrees of polymerization were either 22 or 45 for PEO. In a typical synthesis, PEO (5.0 g) dissolved in 100 mL of dry THF was added to a round-bottomed flask under dry nitrogen. Potassium naphthalene (2.50 mmol) in THF was added via a double-tipped needle, and the reaction solution was stirred at 30° C. for 1-2 h to form the alcoholate macro-initiator. Freshly distilled tertiary amine methacrylate (5-15 mL) was added, and the polymerization was allowed to proceed for 4 h prior to quenching with methanol. In some cases the polymerizations were conducted at 35 or 50° C. Solvent was removed under vacuum, the copolymer was redissolved in dilute HCl, and the water-insoluble naphthalene was removed by filtration. $PEG_{113}$-$PDPA_{71}$ and $PEG_{10}$-$PDPA_{30}$ were obtained in high yields (95-100%). Good control over copolymer molecular weight was obtained.

Example 2

Preparation of Polymersomes

Polymersomes of poly(2-methacryloxyethyl phosphorylcholine)-poly(2-(diisopropylamino)-ethyl methacrylate), (PMPC-PDPA) and polyethylene oxide-poly(2-(diisopropylamino)-ethyl methacrylate) (PEO-PDPA) were made. Both polymersome formulations were formed by mixing the copolymers under acidic conditions in PBS. The pH was then raised and the polymersome dispersion was extruded through a 200 nm mesh and sonicated so as to control their average size.

Example 3

Uptake of MPC, PEG and Mixed Polymersomes into Cells

Figure 1:
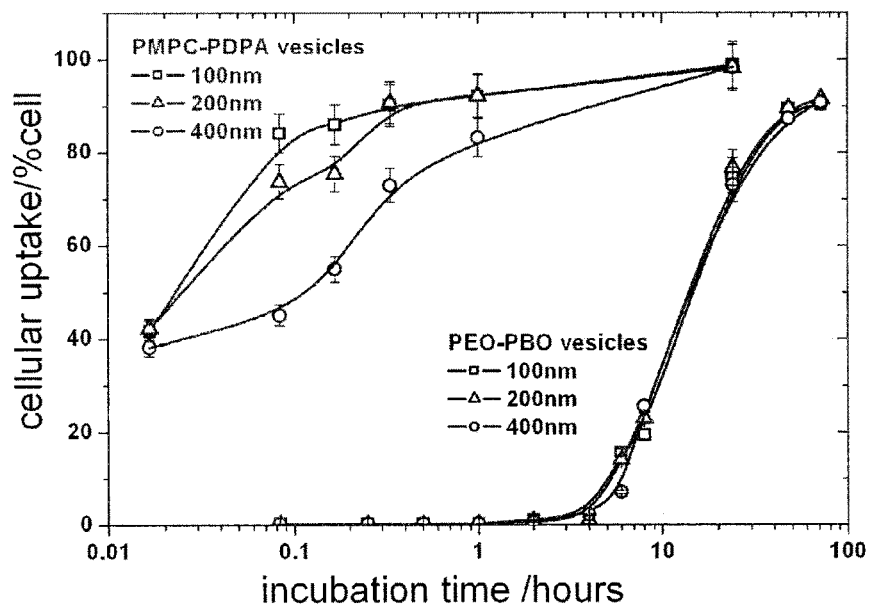
FIG. 1 shows the rate of polymersome uptake in Human Dermal Fibroblast (HDF) cells using flow cytometry.
Figure 2:
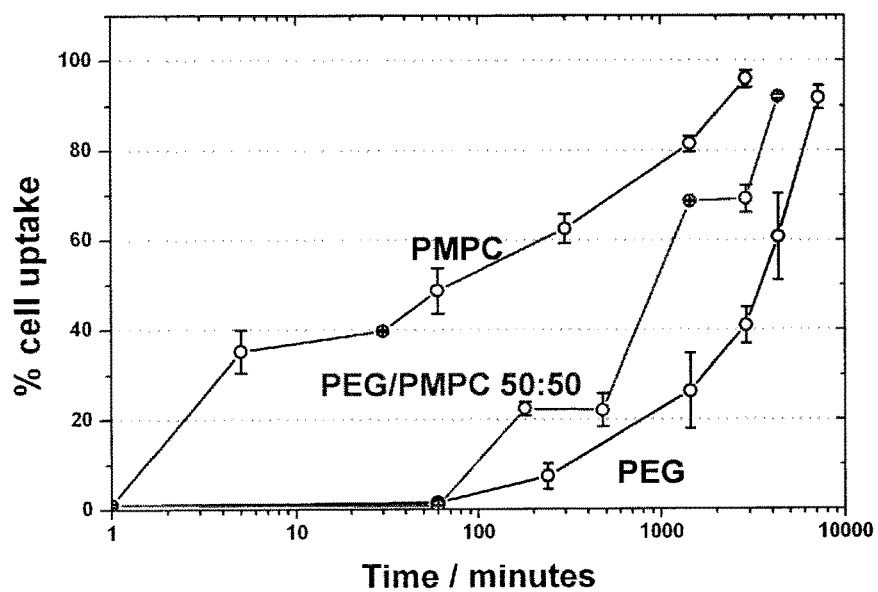
FIG. 2 shows the rate of polymersome uptake by flow cytometry for PMPC polymersomes, PEG polymersomes, and a mixture of MPC and PEG polymersomes.
Figure 3:
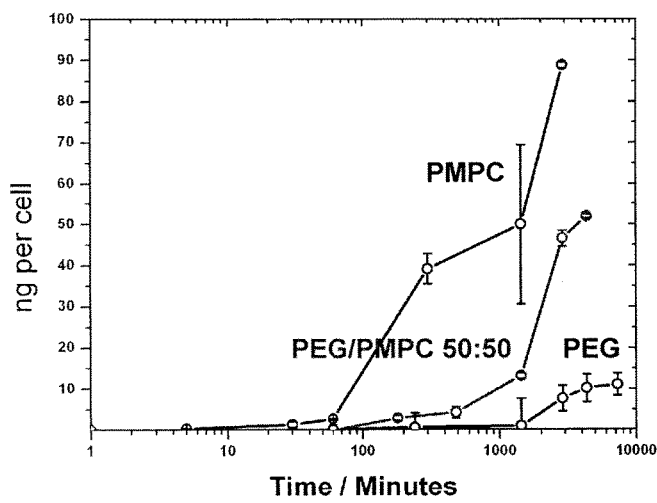
FIG. 3 shows the quantity of polymersome uptake by HDF cells.

Polymersomes of poly(2-methacryloxyethyl phosphorylcholine)-poly(2-(diisopropylamino)-ethyl methacrylate), (PMPC-PDPA), polyethylene oxide-poly(2-(diisopropylamino)-ethyl methacrylate) (PEO-PDPA) and a 50:50 mixture of the two containing rhodamine were made in a variety of sizes by altering the extruder mesh size. The polymersomes were exposed to human dermal fibroblasts and flow cytometry was used to monitor cell uptake of the polymersomes with time. FIG. 1 shows there is a size dependency for PMPC polymersomes but not for PEG polymersomes. The PMPC polymersomes enter the cells extremely rapidly whereas there is a long delay for the PEG polymersomes (FIG. 2). The amount of polymersomes taken up by the cells was determined by cell lyses and spectroscopy and showed there was a much higher uptake of PMPC polymersomes compared to the PEG analogues (FIG. 3). These properties suggest that polymersome systems can be tailored for delivery across epithelia in order to immediately target cells in the upper layers (PMPC rich systems) or allow transport and diffusion through the layers to the lower levels over time by blending with PEG systems.

Example 4

Diffusion of Polymersomes Across Skin

The diffusion across skin of two different pH sensitive polymersomes formulations (PMPC-PDPA and PEO-PDPA) as described in Example 2 was studied in three different models: tissue engineered human and mouse skin, ex-vivo human skin, and in vivo experiments on shaved mice. Polymersome diffusion was monitored by chemically and physically labelling the polymersomes with the fluorescent dye Rhodamine B (as described in Adv. Mater. 2007, 19, 4238-4243). The skin models were exposed to the polymersome dispersion for different times and then analyzed by confocal laser scanning microscopy and cryogenic histology, which showed PMPC-PDPA polymersome diffusion across the skin. The former technique allows a real-time monitoring of diffusion across the skin by simultaneous imaging of the natural autofluorescence arising from the different ECM proteins that comprise the skin and the rhodamine from the polymersomes.

The study on the three different models has shown that polymersomes are able to diffuse across the Stratum Corneum and rapidly cross the basal membrane to the dermis. The diffusion depends on the surface chemistry of the polymersome. Indeed PEG polymersomes have a higher diffusion coefficient than PMPC polymersomes and they more rapidly reach the dermis. PMPC polymersome have, in fact, been observed to interact with the cells and become internalized more efficiently than the PEG analogues.

Example 5

Polymersome Diffusion Through Tissue Engineered Skin

Figure 4:
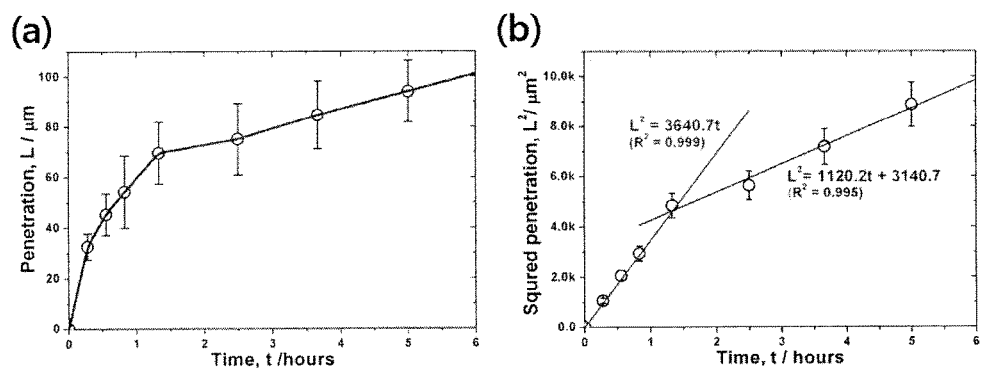
FIG. 4 shows (a) PMPC-PDPA vesicle skin penetration as a function of time; (b) squared skin penetration as a function of time.

A non-destructive technique to visualise nanoparticle diffusion through tissues was used, involving engineered skin tissue which was incubated with a polymersome suspension and then analysed by confocal laser scanning microscopy (CLSM). This microscope allows multifluorescent imaging with sub-micrometer resolution within 3D space. The technique allowed simultaneous 3D visualisation of the living skin in green (skin autofluorescence) and the polymer vesicle diffusion wave in red. It seems that polymersomes penetrate skin tissues according two different regimes: at first relatively rapidly, and then they enter a slower phase (FIG. 4a). This indicates that as the polymersomes reach the epidermal layer they slow down, in accordance with the data obtained from histology. This can be further confirmed by plotting the squared vesicle skin penetration, $L^2$, as a function of time (FIG. 4b). Polymersomes follow a dual Fickian diffusion (i.e. $L^2$ changes linearly with time), and this result suggests that the polymersome diffusion varies according to the part of the skin tissue they have reached.

Example 6

Polymersome Diffusion in 3D Models

Tissue engineered models of oral mucosa mimic in vivo conditions better than cell monolayers. These 3D models are important to enable the study of the behaviour and response of cells in a 3D situation. This Example demonstrates how the penetration of fluorescently labelled polymersomes can be imaged in models of the oral mucosa.

Polymersome Diffusion Across Oral Mucosa

Full thickness tissue engineered oral mucosa is comprised of normal oral keratinocytes and normal oral fibroblasts grown on a de-epidermised dermis (DED) scaffold. These are cultured for up to 2 weeks at an air-liquid interface to encourage organisation. Imaging of the oral mucosa is achieved using confocal laser scanning microscopy.

Polymersomes were avidly internalised and penetrated the epithelial layers of the oral mucosal model in a time-dependent manner. Diffusion through the epidermis could be seen after 6 hours.

Example 7

Rate of Polymersome Diffusion Across Human Skin

Figure 5:
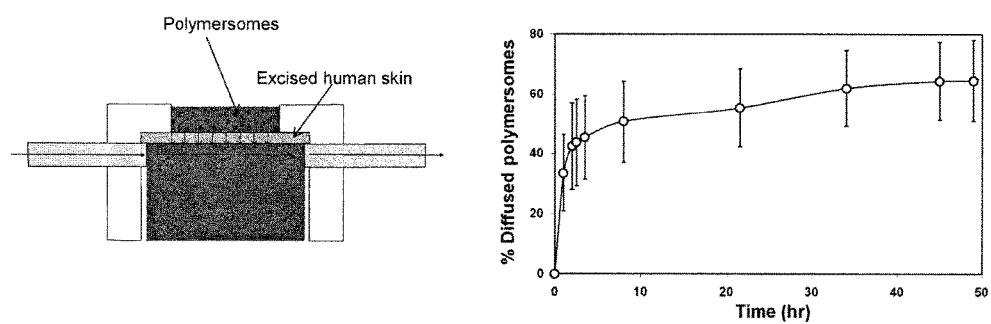
FIG. 5 shows the polymersome diffusion across excised human skin, showing that after 5 hours 50% of the polymersomes have diffused through the skin comprising an intact epithelium and dermis (error bars SD n=3)
Figure 6:
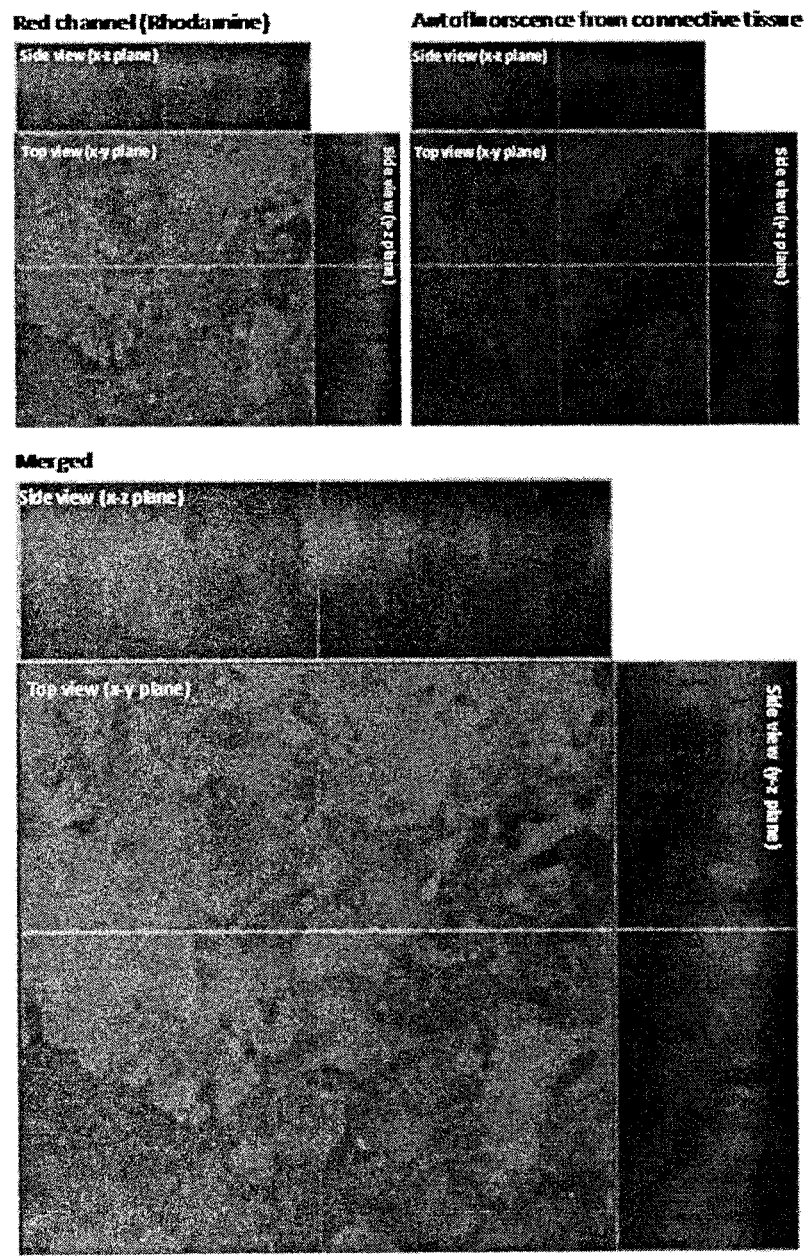
FIG. 6 shows a CLSM image of Polymersome-mediated Delivery of Rhodmine to Tissue Engineered Skin.

Excised human skin comprising an intact epithelium and dermis was placed in a specially designed cell as shown in FIG. 5 in which a continuous circulatory flow of PBS was passed beneath the skin surface and through a UV-visible spectrophotometer, whilst the rhodamine-labelled polymersome solution was placed on the upper surface of the skin. As shown in FIG. 5, the polymersome diffusion across the skin layer could be tracked over time, with ~50% of the polymersomes having diffused through the skin in 5 hours.

Example 8

Polymersome-Mediated Delivery of Rhodamine into Tissue Engineered Skin

Polymersomes were prepared as per Example 2 and loaded with Rhodamine octadecyl ester as described below.

The tissue engineered skin was exposed to the polymersomes for 24 hr and the skin then imaged by confocal laser scanning microscopy, to determine the extent of delivery of the rhodamine into the layers of the skin. The depth of penetration and delivery can be appreciated on the side view (both x-z and y-z planes).

Vesicles Preparation

PMPC-PDPA copolymer was added to a glass vial and dissolved in a solution of 2:1 chloroform: methanol, at a concentration of 4 mg/ml. The solvent was evaporated under vacuum, resulting in a copolymeric film deposited on the walls of the vial. The copolymer film was sterilized in an autoclave and then rehydrated under sterile conditions using phosphate buffer saline (100 mM PBS) to form a 5 mg/ml copolymer suspension. The pH of this suspension was dropped to pH 2 to solubilise the film again and the pH was increased to neutral pH. The dispersion was sonicated and extruded using a LiposoFast with a 200 nm filter membrane.

Amphiphilic and Hydrophobic Fluorescent Marker Encapsulation

The following dye was used: octadecyl ether rhodamine B. This was dissolved in chloroform to form a 0.2 mg/ml solution. Aliquots of this solution were added to the sample of PMPC-PDPA copolymer dissolved in 2:1 chloroform/methanol. The polymersomes were then prepared by film rehydration and sonication, as described above in Example 2.

Example 9a

Encapsulation of Metronidazole into Vesicles

Metronidazole was mixed with the $MPC_{25}$-$DPA_{70}$ at pH2 and then the pH raised to 7 to allow vesicle formation thus encapsulating the drug within its central core. Encapsulated drug was isolated from free drug using size-exclusion chromatography. It was noted that fractions up to 8 mL were clear and had no optical density, and so this was taken as background PBS. However, fractions from 8 mL to 11 mL were turbid showing presence of vesicles. On disruption of the vesicles by lowering the pH, no metronidazole could be detected. After 11 mL the fractions became clear again and metronidazole was detected at 25 to 32 mL which constitutes the free metronidazole fraction. These data suggest that during the fractionation down the column, the drug partitioned out of the vesicles and into the solution (as metronidazole has a negative log P and can diffuse across the vesicle membrane readily). It was therefore assumed that post encapsulation of metronidazole, an equilibrium exists between encapsulated and free drug. For the evaluation of the antimicrobial activity of the encapsulated drug, this unseparated formulation was used and compared to free drug alone to determine the efficacy of the vesicle-encapsulated portion.

Example 9b

Generation of Metronidazole Vesicles for Cellular Invasion Assay

The polymer was prepared as in Example 9a. The film was dissolved by adding 2 ml of sterilized PBS (pH2) until the solution was clear. The concentration of polymer was 10 mg/ml. This was then sterilized using a 0.2 μm filter. The pH of the solution was adjusted to 7.4 with sterilized 1M NaOH and the vesicles purified by gel filtration chromatography using sterilized sepharose agar 4B (Sigma, Poole, Dorset, UK). To encapsulate metronidazole, the diversity of concentration of metronidazole solution was prepared in DMEM: 0.0125, 0.125, 1.25 and 12.5 μg/ml. 200 μl of 10 mg/ml vesicle solution in PBS was re-suspended into 1 ml of metronidazole-DMEM solution to give 0.01, 0.1, 1.0 and 10 μg/ml metronidazole solution respectively with 2 mg/ml vesicles. The solution was then sonicated for 30 minutes to increase the encapsulation efficiency of metronidazole.

Example 9c

Comparing the Effectiveness of Intracellular Antibiotic Drug with Free Drug for Intracellular Killing of *P. gingivalis*

*P. gingivalis* (strain ATCC 11834) invasion assay for H-357 keratinocytes was used in this example, and encapsulated metronidazole was prepared as in Example 9b. After extracellular *P. gingivalis* were removed by 200 μg/ml metronidazole and H357 cells washed 3 times by DMEM, increasing amounts of encapsulated metronidazole in 1 ml DMEM was dispensed in each well for 3 hours at 37° C. with 5% $CO_2$. After that, 200 μl of the medium was collected for H357 viability test using the LDH assay. Moreover, keratinocytes in a different plate treated in an identical manner was tested for H357 viability using propidium iodide and Hoechst. The encapsulated metronidazole was discarded and washed 3 times with DMEM. The cell membranes of H357 were lysed using 0.1% saponin for 5 minutes. Serial dilutions of the lysate were used to determine colony count.

Metronidazole at increasing concentrations was mixed with vesicles (2 mg/ml) at pH2 and then the pH raised to pH7 to encapsulate the metronidazole. This was then sonicated for 30 minutes to improve encapsulation. The mixture was not separated by size-exchange chromatography, so the free metronidazole was in equilibrium with the encapsulated metronidazole. *P. gingivalis* (ATCC 33277) at MOI 100 was used to infect H357 cells for 90 min. These were then washed 3 times with PBS followed by 60 minutes treatment 200 pg/ml metronidazole to kill any extracellular bacteria. Finally, the free/encapsulated metronidazole mixture was added to H357 cells and compared against infected cells treated with free metronidazole, DMEM (no vesicles or antibiotic treatment), vesicles alone (no metronidazole), gentamycin (an antibiotic that does not kill P. gingivalis) and encapsulated metronidazole. Saponin was then used to release intracellular bacteria from H357 cells and the number of intracellular P. gingivalis measured by counting the colonies from serial dilutions.

FIG. 7 shows that a mixture of free and encapsulated metronidazole significantly (p,<0.001 (*), 0.007 (**), 0.020 (*) and 0.006 (**) respectively) reduces the amount of intracellular bacteria compared to DMEM or free metronidazole only, at all concentrations tested. However, the free/vesicle metronidazole mixture did not eradicate all intracellular bacteria. Furthermore, gentamycin was not able to kill the intracellular P. gingivalis in either free or encapsulated form showing that killing of intracellular P. gingivalis is specific to the delivery of metronidazole. In addition, vesicles alone appear to reduce the levels of intracellular bacteria suggesting that this has an effect on P. gingivalis cell viability. This experiment was repeated twice more with similar results except that at lower concentrations (0.01 and 0.1) free and encapsulated metronidazole did not achieve a significant difference compared to free metronidazole alone although inhibition was seen. However, above these concentrations (1 and 10) killing of intracellular P. gingivalis was significant.

The viability of H357 under all the different concentrations of metronidazole, vesicles and gentamycin was also determined using the lactate dehydrogenase assay (FIG. 8). These data show that under all conditions the viability of H357 was not significantly different. Treatment with saponin caused 100% cell death and was used as a positive control. Treatment with free metronidazole or free plus encapsulated metronidazole caused less cell death than the DMEM control.

The invention claimed is:

1. A method of treatment comprising administering to a human or animal body a composition comprising nanovesicles and, encapsulated within the aqueous core of the nanovesicles, a chemical agent, wherein the chemical agent is delivered trans- and/or intra-epithelially to a human or animal body across an epidermis, oral mucosa, buccal cavity or by bronchial delivery, wherein the nanovesicles comprise an amphiphilic block copolymer having a hydrophilic and a hydrophobic block, the hydrophobic block comprises pendant tertiary amine groups which have a $pK_a$ in the range 3.0 to 6.9, the hydrophilic block is formed from ethylenically unsaturated radically polymerisable monomers comprising a zwitterionic monomer, the ratio of the degree of polymerization of the hydrophilic to hydrophobic block is in the range of 1:2.5 to 1:8 and the nanovesicles have a diameter in the range 50-1000 nm, and wherein the chemical agent is delivered into the cell cytosol after the nanovesicles have at least partially crossed the epithelium, wherein the nanovesicles comprise two populations of vesicles, the first of which has a hydrophilic block which is polyalkylene oxide, and the second of which has a hydrophilic block formed from ethylenically unsaturated radically polymerisable monomers comprising a zwitterionic monomer, and wherein the zwitterionic monomer has the general formula, $$Y B X \qquad I$$

in which Y is an ethylenically unsaturated group selected from $H_2C=CR-CO-A-$, $H_2=CR-C_6H_4-A^1-$, $H_2C=CR-CH_2A^2$, $R^2O-CO-CR=CR-CO-O$, $RCH=CH-CO-O-$, $RCH=C(COOR^2)CH_2-CO-O$,

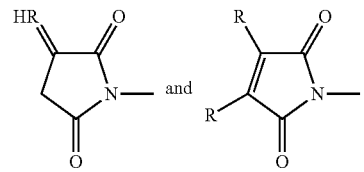

A is —O— or $NR^1$;
$A^1$ is selected from a bond. $(CH_2)_lA^2$ and $(CH_2)_l SO_3^-$ in which l is 1 to 12;
$A^2$ is selected from a bond, —O—, O—CO—, CO—O, CO—$NR^1$—, $NR^1$—CO, O—CO—$NR^1$, $NR^1$—CO—O—;
R is hydrogen or $C_{1-4}$ alkyl;
$R^1$ is hydrogen, $C_{1-4}$ alkyl or BX;
$R^2$ is hydrogen or $C_{1-4}$ alkyl;
B is a bond, or a straight branched alkanediyl, alkylene oxaalkylene, or alkylene (oligooxalkylene) group, optionally containing one or more fluorine substituents;
X is a zwitterionic group.

2. The method according to claim 1, wherein the chemical agent is a pharmaceutically active or a cosmetically active ingredient.

3. The method according to claim 1, wherein one of the blocks comprises pendant groups which have a $pK_a$ in the range 4.0 to 6.9.

4. The method according to claim 1 wherein the hydrophobic block has a degree of polymerisation in the range 50-250, and the hydrophilic block has a degree of polymerisation of at least 15.

5. The method according to claim 1, in which X is a group of the general formula II

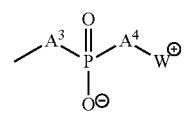

in which the moieties $A^3$ and $A^4$, which are the same or different, are —O—, —S—, —NH— or a valence bond, preferably —O—, and $W^+$ is a group comprising an ammonium, phosphonium or sulphonium cationic group and a group linking the anionic and cationic moieties which is preferably a $C_{1-12}$-alkanediyl group,
preferably in which $W^+$ is a group of formula

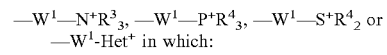

$W^1$ is alkanediyl of 1 or more, preferably 2-6 carbon atoms optionally containing one or more ethylenically unsaturated double or triple bonds, disubstituted-aryl (arylene), alkylene arylene, arylene alkylene, or alkylene aryl alkylene, cycloalkanediyl, alkylene cycloalkyl, cycloalkyl alkylene or alkylene cycloalkyl alkylene, which group $W^1$ optionally contains one or more fluorine substituents and/or one or more functional groups; and
either the groups $R^3$ are the same or different and each is hydrogen or alkyl of 1 to 4 carbon atoms, preferably methyl, or aryl, such as phenyl, or two of the groups $R^3$ together with the nitrogen atom to which they are attached form an aliphatic heterocyclic ring containing from 5 to 7 atoms, or the three groups $R^3$ together with the nitrogen atom to which they are attached as heteroaromatic ring having 5 to 7 atoms, either of which rings may be fused with another saturated or unsaturated ring to form a fused ring structure containing from 5 to 7 atoms in each ring, and optionally one or more of the groups $R^3$ is substituted by a hydrophilic functional group, and the groups $R^4$ are the same or different and each is $R^3$ or a group $OR^3$, where $R^3$ is as defined above; or Het is an aromatic nitrogen-, phosphorus- or sulphur-, preferably nitrogen-, containing ring, for example pyridine.

6. The method according to claim 1, in which the zwitterionic monomer is 2-methacryloyloxyethylphosphorylcholine.

7. The method according to claim 1, in which the hydrophobic block is formed by radical polymerisation of ethylenically unsaturated monomers.

8. The method according to claim 7, in which the monomers from which the hydrophobic block is formed have the general formula VII $$Y^1B^1Q \qquad \qquad VII$$

in which $Y^1$ is an ethylenically unsaturated group selected from $H_2C$=$CR^{40}$—CO-$A^8$-, $H_2C$=$CR^{14}$—$C_6H_4$-$A^9$-, $H_2C$=$CR^{14}$—$CH_2A^{10}$, $R^{16}O$—CO—$CR^{14}$=$CR^{14}$—CO—O, $R^{14}CH$=CH—CO—O—, $R^{14}CH$=C($COOR^{16}$)$CH_2$—CO—O,

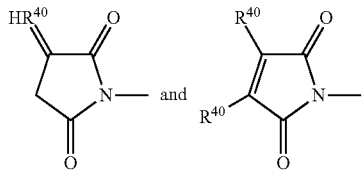
and $A^8$ is —O— or $NR^{15}$;

$A^9$ is selected from a bond, $(CH_2)_qA^{10}$ and $(CH_2)_q SO_3^-$ in which q is 1 to 12;

$A^{10}$ is selected from a bond, —O—, O—CO—, CO—O—, CO—$NR^{41}$—, $NR^{41}$—CO, O—CO—$NR^{15}$—, $NR^{15}$—CO—O—;

$R^{14}$ is hydrogen or $C_{1-4}$ alkyl;

$R^{15}$ is hydrogen, $C_{1-4}$ alkyl or $B^1Q$;

$R^{16}$ is hydrogen or $C_{1-4}$ alkyl;

$B^1$ is a bond, or a straight branched alkanediyl, alkylene oxaalkylene, or alkylene (oligooxalkylene) group, optionally containing one or more fluorine substituents; and Q is a cationic or cationisable group of the formula —$NR^{17}_p$, —$PR^{17}_p$ and $SR^{17}_r$, in which p is 2 or 3, r is 1 or 2, the groups $R^{17}$ are the same or different and each is selected from the group consisting of hydrogen, $C_{1-24}$ alkyl and aryl, or two of the groups $R^{17}$ together with the heteroatom to which they are attached from a 5 to 7 membered heterocyclic ring or three $R^{17}$ groups together with the heteroatom to which they are attached form a 5 to 7 membered heteroaromatic ring, either of which rings may be fused to another 5 to 7 membered saturated or unsaturated ring, and any of the $R^{17}$ groups may be substituted by amino or hydroxyl groups or halogen; wherein if p is 3, at least one of the groups $R^{17}$ must be hydrogen.

9. The method according to claim 1, wherein the hydrophobic block is (diisopropyl)aminoethyl methacrylate (DPA) or (diethyl)aminoethyl methacrylate (DEA).

10. The method according to claim 1, wherein the transepithelial delivery is delivery across an epidermis.

11. The method according to claim 1, wherein one of the blocks is pH-sensitive.

* * * * *